United States Patent [19]

Samir Amer et al.

[11] Patent Number: 5,013,552

[45] Date of Patent: May 7, 1991

[54] MODIFIED POLLEN GRAINS FOR DELIVERING BIOLOGICALLY ACTIVE SUBSTANCES TO PLANTS AND ANIMALS

[76] Inventors: Moh. Samir Amer, P.O. Box 1439, Santa Barbara, Calif. 93102; Rashad Tawashi, 66 Hyde Park, Beaconsfield, Quebec, Canada, H9W 5L8

[21] Appl. No.: 306,170

[22] Filed: Feb. 6, 1989

[51] Int. Cl.⁵ .................. A61K 37/26; A61K 9/50; A61K 31/715; A01N 25/34

[52] U.S. Cl. .................. 424/408; 424/484; 424/499; 424/449; 424/451; 424/434; 424/465; 424/91; 514/3

[58] Field of Search .................. 424/195.1, 74, 91, 10, 424/484, 408, 499, 449, 451, 434, 465; 449/49; 47/1.41; 514/3

[56] References Cited

U.S. PATENT DOCUMENTS

| | | | |
|---|---|---|---|
| 2,150,131 | 5/1937 | Rockwell | 424/91 |
| 2,207,415 | 1/1938 | Rosenwald | 424/91 |
| 2,500,145 | 3/1950 | Ferguson | 424/91 |
| 2,669,066 | 2/1954 | Antles | 426/72 |
| 4,426,397 | 1/1984 | Schanze | 426/72 |
| 4,529,612 | 7/1985 | Robson | 426/641 |

FOREIGN PATENT DOCUMENTS

| | | |
|---|---|---|
| 3533864 | 4/1986 | Fed. Rep. of Germany . |
| 3605050 | 8/1986 | Fed. Rep. of Germany . |
| 038813A | 12/1984 | Hungary . |
| 59-025671 | 2/1984 | Japan . |

*Primary Examiner*—Lester L. Lee
*Assistant Examiner*—Carmen B. Pili Curtis
*Attorney, Agent, or Firm*—Samson B. Leavitt; Michael A. Leavitt

[57] ABSTRACT

Loaded pollen grains are disclosed which are suitable for use as delivery systems for introducing biologically active substances into or on plants and animals. Such pollen grains are suitable to deliver both small and large (macromolecules) molecules. Preferred pollen grains are those that have been defatted and then pre-treated to be free of antigenic materials and that have special surface features that facilitate their attachment to tissue surfaces, particularly to mucous membranes. The most preferred pollen grains are those that have spiny or irregular or fragmented surfaces. Also disclosed are a method of pre-treating the pollen grains to remove antigenic materials; a method of loading the pollen grains with the biologically active material; and a method of incorporating such pre-treated, loaded pollen grains into formulations or dosage forms suitable for introduction into or on a plant or animal body.

6 Claims, No Drawings

MODIFIED POLLEN GRAINS FOR DELIVERING BIOLOGICALLY ACTIVE SUBSTANCES TO PLANTS AND ANIMALS

FIELD OF THE INVENTION

This invention relates to new and improved carriers or vehicles for the delivery of biologically active substances of varying molecular sizes into or on plants and animals (typically humans). It also relates to providing the prolonged release of such substances to the appropriate target organs and bodies.

BACKGROUND OF THE INVENTION

Historically, many methods have been developed to improve the delivery of drugs to their target organs with greater organ specificity, to allow drug release over longer periods of time, and to provide special release characteristics. These controlled drug release methods generally involved the use of carrier systems to carry the drug to the vicinity of its target organ and then to release it in a predetermined fashion. These prior art carrier systems employed a number of substances such as a variety of lipids and phospholipids (liposomes), biodegradable and non-biodegradable polymers, mechanical devices, magnets, ultrasound, osmotic systems, and many others. These systems, however, suffered from several drawbacks.

For example, none of these systems have the intrinsic ability to attach themselves to target organs long enough to allow for localized drug release over prolonged periods of time. None of these systems aid in the absorption of the drug or drugs contained therein into the blood stream. These systems are also limited in the molecular size of the biologically active substances they can deliver, since higher molecular weight proteins and other macromolecules are difficult to load into and release from these systems or devices. Such systems have further generally involved problems of incompatibility or reactivity of the carrier or vehicle with the drug, the prevailing environment and/or target organ or body.

OBJECTS OF THE INVENTION

It is, accordingly, an object of this invention to provide a system or vehicle capable of delivering to target organs and bodies biologically active substances, including chemicals, drugs and other pharmacologically active materials which will not be subject to such drawbacks. Another object is to provide such delivery systems or vehicles capable of delivering over prolonged periods of time such biologically active substances comprised of molecules ranging in size from small to large (i.e., proteins and other macromolecules). A further object is the provision of methods for preparing and loading such delivery systems, carriers or vehicles in a manner that ensures their appropriate and, where desired, prolonged release. Other objects and advantages will appear as the description proceeds.

SUMMARY OF THE INVENTION

The attainment of one or more of such objects is made possible by this invention which includes a composition of matter comprising a pollen grain loaded with a biologically active substance, which loaded substance is releasable in or on a plant or an animal and is foreign to a naturally occurring pollen grain. The invention also includes the method of preparing such composition, comprising extracting at least a portion of extractable material from a naturally occurring pollen grain and substituting at least a portion of the extracted material by a biologically active substance releasable from such pollen grain in or on a plant or animal. The invention is, in part, based on the discovery that pollen grains can be modified by loading therein a variety of biologically active materials, such as drugs, chemicals and other pharmacologically active substances, which can then be delivered to target organs, surfaces or areas in or on plants and animals, where the substance contained within the pollen grains is released. The use of loaded pollen grains as delivery vehicle is particularly useful in the transfer of molecules, and especially large macromolecules, into the animal (e.g. human) blood stream, since they usually cannot otherwise be absorbed therein or reach the circulatory system. Moreover, when such loaded pollen grains are to be administered to animals, it is preferred that they first be defatted and then treated to remove antigenic (e.g. proteins) materials prior to loading.

This invention, thereof, is directed to the use of modified pollen grains that are suitable for use as delivery vehicles for introducing biologically active substances, including drugs, chemicals and other pharmacologically active substances into or on plants and into the bodies of humans or animals. Such pollen grains are suitable to deliver both small and large (macromolecules) molecules. Preferred pollen grains are those that have rough or rugged surfaces that facilitate their attachment to tissue surfaces, particularly to mucous membranes. Most preferred are those pollen grains that have spiny or irregular or fragmented surfaces. Also disclosed are a method of pre-treating the pollen grains to remove antigenic materials; a method of loading the pollen grains with biologically active materials; and a method of incorporating such pre-treated, loaded pollen grains into formulations or dosage forms suitable for introduction into or on a plant or animal body.

In general, this invention provides modified pollen grains having biologically active substances loaded therein, which substances are foreign to naturally occurring pollen grains and have been loaded therein for the express purpose of being released at a later time in the appropriate environment.

This invention uses such modified pollen grains to deliver loaded substances having biological activity to target receptacles or organs of plants and animals.

This invention also optimally provides for the prolonged and controlled release of such loaded substances in or on plants and animals.

This invention, as indicated above, further provides a method of loading biologically active substances into pollen grains.

DETAILED DESCRIPTION OF THE INVENTION

Pollen grains have served as delivery vehicles for their naturally-contained genetic material and allergenic proteins throughout the ages. They are, in fact, natural delivery devices for macromolecules the size of proteins and nucleic acids, as well as for smaller molecules. In cross-section, a pollen grain resembles a sponge and has an extremely large surface area. Most pollen grains are also characterized by rugged surfaces that cause them to adhere to and, optimally, to produce micro-surgical cuts in mucous membranes and other target surfaces. These properties can be taken advantage of by loading pollen grains with a variety of biologically active materials, such as chemicals, drugs, and pharmacologically active substances, which can then be delivered to the target organs in plants (which term is used in its broadest sense and includes trees, shrubs, grass, flowers, fruit and vegetable plants, weeds, etc.) or animals, where the loaded substance contained within the pollen grains is released. Since the rugged surface of each pollen grain adheres to tissue surfaces and particularly to mucous membranes, the loaded pollen grains are assured of remaining in contact with the target organ for prolonged periods of time. Optimally, micro-surgical cuts in mucous membranes also result from the surface ruggedness and/or spiny surfaces of pollen grains, whereby the transfer of the loaded substances contained therein to the blood stream or circulatory system will be enhanced. Thus, the use of pre-loaded pollen grains as delivery vehicles is particularly useful in the transfer of molecules, and especially large macromolecules, into the blood stream, since they cannot otherwise usually be absorbed therein or reach the circulatory system. That molecules, including large allergenic proteins, can be released from pollen grains into the bloodstream is well-known, as can be evidenced by the allergenic proteins found naturally therein that are released into the blood and cause allergic reactions in sensitive individuals.

Pollen grains are specialized structures that house the sperm or male gametes of flowering plants. Pollen grains generally comprise two or three cells combined as a unit. Typically, each cell contains as substantially extractable components about 20% protein, 37% carbohydrate, 4% lipids or natural oils, and 3% minerals. The cellulose walls of pollen grains, which constitute about the remaining 36%, are so tough that they resist degradation by hot concentrated acids and hot alkalis, the ravages of time (as evidenced by fossilized pollen grains), and grinding in a blender. They are, however, edible.

Pollen grains, which can be obtained commercially from The Greer Laboratories Corporation of Lenoir N.C., are classified by source, namely, grasses, weeds, trees, shrubs, flowers (wild and cultivated), and cultivated farm plants. They are available both as whole, dry grains with natural oils or as defatted grains. As previously mentioned, in cross-section, pollen grains resemble sponges and have extremely large surface areas. Many are also characterized by rugged external surfaces or shells, some of which are spiny. They are stable to temperature and chemical treatment within reasonable limits.

The spiny-surfaced pollen grains of ragweed, paper mulberry (Broussonetia papyrifera), and corn (Zea mays) are especially preferred in the practice of this invention. For example, ragweed pollen has such a spiny surface that facilitates attachment to mucous membranes and other target surfaces and produces the microsurgical cuts therein. It is spherical in shape and about 17–21μ in size. However, many other pollen grains with suitable surface characteristics can also be used. Again, these characteristics relate to the shells, which, most preferably, should be spiny surfaces or otherwise rugged in nature (determinable by fractal geometry), which cause them to adhere to tissue surfaces, especially to mucous membranes, to provide prolonged contact and micro-surgical cuts, resulting in more effective release of the pre-loaded material contained therein and absorption into the bloodstream or target organ. Thus, the following pollen grains, which have spiny shells, represent other preferred materials: Cocklebur (*Xanthium commune*); Goldenrod (*Solidago spp.*); Poverty weed (*Iva axillaris*); Desert Ragweed (*Ambrosia dumos*); False Ragweed (*Ambrosia acanthicarpa*); Giant Ragweed (*Ambrosia trifida*); Short Ragweed (*Ambrosia artemisifolia*); Slender Ragweed (*Ambrosia tenuifolia*); Southern Ragweed (*Ambrosia bidentata*); Western Ragweed (*Ambrosia psilostachya*); Prairie Sage (*Artemisia ludoviciana*); Common Sagebrush (*Artemisia tridentate*); Annual Wormwood (*artemisia annua*); Marsh Elder; and High-Water Shrub.

To ensure safety in the administration to animals, especially humans, of the pre-loaded pollen grains of this invention, the grains are first treated to be free of antigenic materials. Thus, the risk of allergic reaction or anaphylactic shock is greatly reduced. It will be noted that all humans are exposed to pollen grains, but only those sensitive to their allergenic contents react.

The method of the invention involves subjecting the natural pollen grain to an extraction process, i.e. treatment with a material, usually a liquid, which dissolves, reacts with, decomposes or breaks down a component contained in the cellulose shell of the pollen grain to permit such component to be removed, i.e. extracted therefrom. The lipid, fat or oil component is generally extracted with an organic solvent, preferably ethylether, although any other suitable volatile organic solvent may be employed, such as petroleum ether, acetone, hexane, benzene, toluene, kerosene, chloroform, carbon tetrachloride, diethyl formamide, etc. The same component may, for example, be alternatively removed by saponification, i.e. treatment with alkali. This defatting procedure is however well known, defatted pollen grains being in fact commercially available. Since removal of antigenic components from the pollen grain is usually not necessary when the intended use is for plants, the defatted pollen grain may in accordance with one aspect of the invention be without further treatment loaded with any desired biologically active plant treating substance, such as herbicides, insecticides, larvicides, nematocides, pesticides, growth regulators and the like, and the loaded pollen grains applied to the plants in any desired manner as by dusting, spraying, irrigating, etc. or even by natural pollination methods using bees, for example, to transmit the loaded pollen grain to the plant.

For animal use, defatting is also generally necessary since its presence in the pollen grain interferes with the desired extraction or removal of the antigenic, proteinaceous and other components of the pollen grain. The remaining non-fat components of the pollen grain may be similarly extracted preferably by treatment with room temperature and/or hot water and/or alcohol liquids, alternatively and/or successively as needed. Desirably, saline, preferably isotonic, extraction solutions may be employed successively at room and elevated temperatures followed by repeated washing as with water and/or alcohol, drying and autoclaving at elevated temperatures and pressures to assure completion denaturization of the antigenic protein and sterilization of the extracted pollen grain. This treatment effectively removes substantially all the original non-fat components of the pollen grain. In some instances, extraction treatment with ethylether or other suitable volatile organic solvent as described above may effectively remove selected non-fat components.

Illustrative pre-treatment of pollen grains: Commercially available defatted pollen grains are extracted in a continuous extractor with isotonic saline (0.9% NaCl) for 12 hours. The pollen grains are then filtered and extracted continuously for another 12 hours using hot isotonic saline (50-60 degrees C.). These extractions should be sufficient to remove any antigenic proteins or other foreign materials other than the cellulose shell. The Ninhydrin test can be used to test for any residual proteins. The pollen grains are then filtered, washed 2-3 times with deionized water, 2-3 times with alcohol and dried (at 80°-90° degrees C.) for 1-4 hours. Other organic solvents suitable for extraction include those described above. Drying, in addition to removing excess water, will also denature any antigenic proteins that escaped extraction. The extracted and dried pollen grains are then autoclaved (at 15 lbs. pressure and 121 degrees C. for about 30 minutes) to further assure denaturization and sterilization. After cooling, the pretreated pollen grains are then ready to be used to load the drug, chemical, or other biologically active substance.

Illustrative loading with the drug substance: The extracted and dried pollen grains are put in a vacuum chamber (@ about 50 mm. Hg) and a concentrated dispersion, e.g. solution (preferred), suspension, or emulsion, of the biologically active drug, chemical or other pharmacologically active substance in a volatile solvent or otherwise removable liquid carrier is introduced. The concentration of the material used will depend on its nature, solubility and the amount of the material to be loaded per mg. of pollen grains, and may be from about 5–40% by weight. The loading treatment is generally conducted to deposit about 5–50%, preferably about 10–30%, of the biologically active substance by weight of the loaded pollen grains, but not such as to cover the surface of the pollen grain as to effectively obliterate the spines or rugged nature of the said surface. After loading, the pollen grains are dried and may be washed once with deionized water (if the substance is water insoluble) before inclusion into the final dosage form to be administered.

Illustrative preparation of the final form to be administered: Any treatment of the loaded pollen grains will depend primarily on the stability and other properties of the drug, chemical or other biologically active substance used. As previously mentioned, pollen grain shells are composed primarily of cellulose, and they are stable to temperature and chemical treatment within reasonable limits. If the chosen substance is sensitive to heat, or elevated or reduced pH's, then treatment of the pollen grains would avoid elevated temperatures, extreme variations in pH, or any other variable that would be detrimental to the activity of the loaded substance.

A wide variety of biologically active substances, as illustrated below, may be loaded into the pollen grains of this invention. They include simple and complex chemicals, drugs, and other pharmacologically active substances.

Examples of drugs include

Anaesthetics, local: Xylocaine, eugenol, et.

Analgesics: Ibuprofen, et.

Antibacterials

Antibiotics: Neomycin, tetracycline, etc.

Anti-cariogenic drugs; Fluorides (for use in toothpastes), etc.

Anti-inflammatory drugs: Cortisone acetate, prednisolone, etc.

Anti-viral agents

Aromatics: Cinnamon, clove oil, etc.

Biocides

Cytotoxics (for local anti-tumor therapy): Mitomycin, etc.

Flavoring agents: Menthol (in toothpaste), etc.

Hormones

Proteins and peptides: Insulin, calcitonin, etc.

Steroids

Examples of biologically active substances for plant treatment include

Herbicides: 2,4-D; 2,4,5-T; TCDD; alachlor; amiben; barban; diuron; paraquat; propanil; propham; etc.

Insecticides: Benzyl benzoate, organophosphorous compounds, etc.

Lavricides: Synthetic pyrethroids, etc.

Nematocides

Pesticides: DDT, aldrin, benzene hexachloride, chlordane, dieldrin, heptachlor, methyl bromide, phosphine, rotenone, etc.

Plant Growth Regulators

The exact dosage form (tablet, suspension, parenteral, inhalant, cream, etc.) will depend on the pharmacodynamic and pharmacokinetic properties of the drug to be loaded. The release characteristics of the loaded substance to or in the target body are very similar to first order kinetic release and depend, among other things, on the solubility of the substance in the environment under question and the degree of solvent access to the loaded pollen.

Moreover, the loaded pollen grains of this invention can be incorporated into any type of pharmaceutical formulation or dosage form for administration to humans or animals, including aerosols, buccal and sublingual tablets, oral tablets, capsules, caplets, surgical implants, lozenges, nasal sprays, creams and ointments, injectables, parenterals, transdermal patches, liquids, mouthwashes, nose drops, dental floss, and the like. They can also be enteric coated.

They can also be used to introduce substances into or on plants by pollination.

The following examples illustrate the best modes contemplated for carrying out this invention. All amounts and proportions are by weight and temperatures are in degrees C as referred to herein and the appended claims unless otherwise indicated.

EXAMPLE I (a) 100 grams of pollen grains are first dried at 55–60 degrees C. for 24 hours in a hot air oven. (b) The dried pollen grains are then defatted by extraction with anhydrous ethyl ether, using a magnetic stirrer for 12 hours. Each 1 gm. of pollen is extracted with 50 cc. of ethyl ether. The process is repeated 2–3 times at room temperature. (c) The defatted pollen is then extracted with normal physiological solution (isotonic saline, which is 0.9% NaCl) for 12 hours, again using a magnetic stirrer, employing 100 ml. for each 2 gm. of pollen, at room temperature followed by similar extraction with hot isotonic saline. Separation in steps (b) and (c) is accomplished by simple filtration through a0.45$\mu$ Millipore filter under vacuum. (d) The pollen grains are then washed 2–3 times with deionized water and again with 95% alcohol to desalt the pollen grains. They are then dried at 90 degrees C. for 2–4 hours in a hot air oven. (e) The extracted, washed, and dried pollen grains are then autoclaved at 121 degrees C. for 30 minutes at 15 lbs. pressure, transferred to a vacuum dessicator (@ about 5 mm. Hg) and stored for 24 hours at room temperature before loading with a drug. This step (e) and the preceding drying step individually and collectively assure the denaturing of any residual proteins and the sterilization thereof. The drug to be loaded is then dissolved, suspended or emulsified in an appropriate generally volatile aqueous or nonaqueous solvent or other liquid carrier, and the resulting solution, suspension or emulsion typically of 10-20% concentration is added to the pollen. Loading is performed under vacuum (for about an hour) at 5 mm. Hg pressure. The loaded pollen drug carrier is later dried (at 45-50 degrees C. for 24 hours or at lower temperatures under vacuum for heat-sensitive drugs, such as proteins). The loaded pollen drug carrier can now be introduced into a suitable formulation or dosage form to provide the controlled, prolonged release of the drug contained therein.

EXAMPLE II 100 grams of ragweed pollen grains are defatted with three consecutive 500 ml. portions of anhydrous diethyl ether. The defatted pollen grains are allowed to dry at room temperature until free of an ether smell (6-24 hours). The pollen grains are then extracted in a continuous extractor with isotonic saline (2-3 liters) for twelve hours. The process is repeated with hot (50-60 degrees C.) isotonic saline for another twelve hours. The pollen grains are then filtered and washed three times with 500 ml. portions of deionized water, followed by similar treatment with absolute alcohol and then dried in a hot air oven (85-90 degrees C. for 1-4 hours). The pollen grains are then autoclaved (15 lbs. pressure at 121 degrees C. for thirty minutes). After cooling, the pollen grains are placed in a vacuum chamber together with a 20% solution of insulin in water. After a good vacuum is obtained (about 50 mm. Hg), the insulin solution is mixed well with the pollen grains. After equilibration, the vacuum is released. The pollen grains are then filtered and lyophilized at low temperature and pressure (below 0 degrees C. temperature and below 50 mm. Hg pressure) to remove the excess liquid. When all the water is removed, the loaded pollen grains are ready for use.

EXAMPLE III

Tablets are comprised of the following ingredients:

| | |
|---|---|
| Avicel Ph. 102 (Carboxymethylcellulose & microcrystalline cellulose) | 70 mg. |
| Cabosil (Silica) | 0.2 mg. |
| Magnesium stearate | 0.5 mg. |
| Pollen drug carrier | 10 mg. |
| Mannitol | to 100 mg. |

Preparation: The tablet is prepared by mixing of the ingredients and by direct compression of the mixture into 100 mg. tablets. Each tablet, which disintegrates in less than 20 seconds, contains 2 mg. or 48 units of insulin. The pollen drug carrier is prepared by the addition of porcine, soluble insulin in a buffered aqueous solution at a pH of 7 and at a concentration of 20 mg./ml. to 80 mg. of pre-treated pollen. The pre-treating (extraction) of the pollen grains and the loading of the insulin therein are accomplished in accordance with the procedures discussed in Examples I and II above. Water is then removed by lyophilization (freeze-drying) or vacuum evaporation (at 0.5 mm. Hg and at 10 degrees C.).

Generally speaking, this invention is directed to a composition of matter comprising a pollen grain that has been modified by loading therein a biologically active substance, which loaded substance is releasable in or on a plant or animal and is foreign to a naturally occurring pollen grain. It is further directed to a method of modifying a pollen grain to render it capable of delivering into or on plants and animals a loaded substance foreign to a naturally occurring pollen grain. The method generally comprises the steps of: defatting the pollen grain; extracting by solvent means at least a portion of the extractable materials normally found in the pollen grain; modifying the defatted and extracted pollen grain by loading the substance therein; and incorporating at least a portion of the loaded pollen grains into a form suitable for introduction into or on plants, or into humans or animals. It should be pointed out that the defatting step may not be necessary if the loaded pollen grains are to be used in plants. In such a case, the extraction step will be needed to remove only a sufficient amount or volume of the extractable materials normally found in a naturally occurring pollen grain to provide room for the amount of material to be loaded therein.

It will be understood that the foregoing discussion, as completed by the specific examples, only illustrates the invention and its principles. However, many modifications and variations in the details of the disclosure will occur to those skilled in the art to which this invention relates and still remain within the scope and principles of the invention. For example, the illustrative embodiments of the invention deal primarily with loading drugs into pre-treated pollen grains. It is apparent, however, that the principles of the invention can be applied to loading the other drugs, chemicals, and biologically active substances mentioned above. Broadly considered, though, the principles of this invention apply to the use of modified pollen grains to deliver substances loaded therein, which substances are foreign to naturally occurring pollen grains and have been loaded therein for the express purpose of being released at a later time in the appropriate environment. More specifically, this invention applies to the specific use of modified pollen grains to deliver substances having biological or pharmacological activity loaded therein to target receptacles or organs of plants, humans, or animals. It further applies to providing the prolonged and controlled release of the loaded substance, as well as to the method of loading the substance into the pollen grains. In essence, therefore, this invention relates to the providing of "reservoirs" for the prolonged and controlled release of drugs, chemicals and other biologically or pharmacologically active substances into plants and the bodies of humans and animals. Finally, it applies to removing at least a portion of naturally occurring extractable substances from, preferably, defatted pollen grains and subsequently replacing them (loading) with biologically active substances such as drugs, chemicals, and other pharmacologically active substances and administering such loaded pollen grains to plants, humans or to animals.

This invention has been disclosed with respect to preferred embodiments, and it will be understood that variations and modifications thereof may be made by those skilled in the art, and they are intended to be included within the spirit and purview of this application and the scope of the appended claims.

What is claimed is:

1. A composition of matter comprising original cellulose shells of pollen grain the pores of which are internally loaded with about 5% to about 50% by weight of a biologically active substance, said loaded substance being releasable in or on a plant or animal, said loaded substance being foreign to the naturally occurring pollen grain.

2. The composition of claim 1 wherein said loaded substance is selected from the group consisting of herbicides, larvicides, plant growth regulators, nematocides and pesticides.

3. The composition of claim 1 wherein said pollen grain is selected from the group consisting of ragweed, paper mulberry, corn, cocklebur, goldenrod, poverty weed, desert ragweed, false ragweed, giant ragweed, short ragweed, slender ragweed, southern ragweed, western ragweed, prairie ragweed, common sagebrush, annual wormwood, marsh elder, and high-water shrub.

4. The composition of claim 1 wherein said loaded substance is selected from the group consisting of anesthetics, analgesics, antibacterials, antibiotics, anti-cariogenics, antiinflammatories, anti-viral agents, aromatics, biocides, cytotoxics, flavoring agents, hormones, proteins and peptides, steroids and mixtures thereof.

5. The composition of claim 4 wherein the loaded substance comprises insulin.

6. The composition of claim 1 wherein said pores are internally loaded with about 10% to about 30% by weight of the biologically active substance.

* * * * *